(12) United States Patent
Kaneko et al.

(10) Patent No.: US 8,755,487 B2
(45) Date of Patent: Jun. 17, 2014

(54) DIFFRACTION GRATING AND ALIGNMENT METHOD THEREOF, AND RADIATION IMAGING SYSTEM

(75) Inventors: Yasuhisa Kaneko, Kanagawa (JP); Hiroyasu Ishii, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 557 days.

(21) Appl. No.: 13/016,978

(22) Filed: Jan. 29, 2011

(65) Prior Publication Data

US 2011/0243300 A1 Oct. 6, 2011

(30) Foreign Application Priority Data

Mar. 30, 2010 (JP) .................. 2010-077168
Sep. 28, 2010 (JP) .................. 2010-216753

(51) Int. Cl.
*A61B 6/00* (2006.01)
(52) U.S. Cl.
USPC .................. 378/62; 378/36; 378/82
(58) Field of Classification Search
CPC .................................................. A61B 4/484
USPC .................. 378/36, 62, 82, 205, 207
See application file for complete search history.

(56) References Cited

U.S. PATENT DOCUMENTS

| 7,180,979 B2 | 2/2007 | Momose | |
| 7,924,973 B2 * | 4/2011 | Kottler et al. | 378/36 |
| 2011/0013743 A1 * | 1/2011 | Nakamura et al. | 378/62 |

FOREIGN PATENT DOCUMENTS

| JP | 2008-200359 A | 9/2008 |
| WO | WO 2004/058070 A | 7/2004 |

OTHER PUBLICATIONS

C. David, et al. "Differential x-ray phase contrast imaging using a shearing interferometer" Applied Physics Letters, vol. 81, No. 17, Oct. 2002, pp. 3287-3289.
Hector Canabal, et al., "Improved phase-shifting method for automatic processing of moiré deflectograms" Applied Optics, vol. 37, No. 26, Sep. 1998, pp. 6227-6233.

* cited by examiner

*Primary Examiner* — Glen Kao
(74) *Attorney, Agent, or Firm* — McGinn IP Law Group, PLLC

(57) ABSTRACT

An X-ray imaging system includes first to third absorption gratings. Initially, the third absorption grating is disposed in a Z axis orthogonal to a detection surface of a FPD, and the position of the third absorption grating is adjusted in θx and θy directions based on a dose of X-rays having passed through the third absorption grating. Then, the first absorption grating is disposed in the Z axis so as to produce a moiré pattern. The position of the first absorption grating is adjusted in the θx and θy directions so that a frequency of the moiré pattern detected by the FPD becomes uniform. Then, the position of the first absorption grating is adjusted in a Z or θz direction so that the FPD loses the detection of the moiré pattern. After that, the second absorption grating is aligned in a like manner as the first absorption grating.

6 Claims, 16 Drawing Sheets

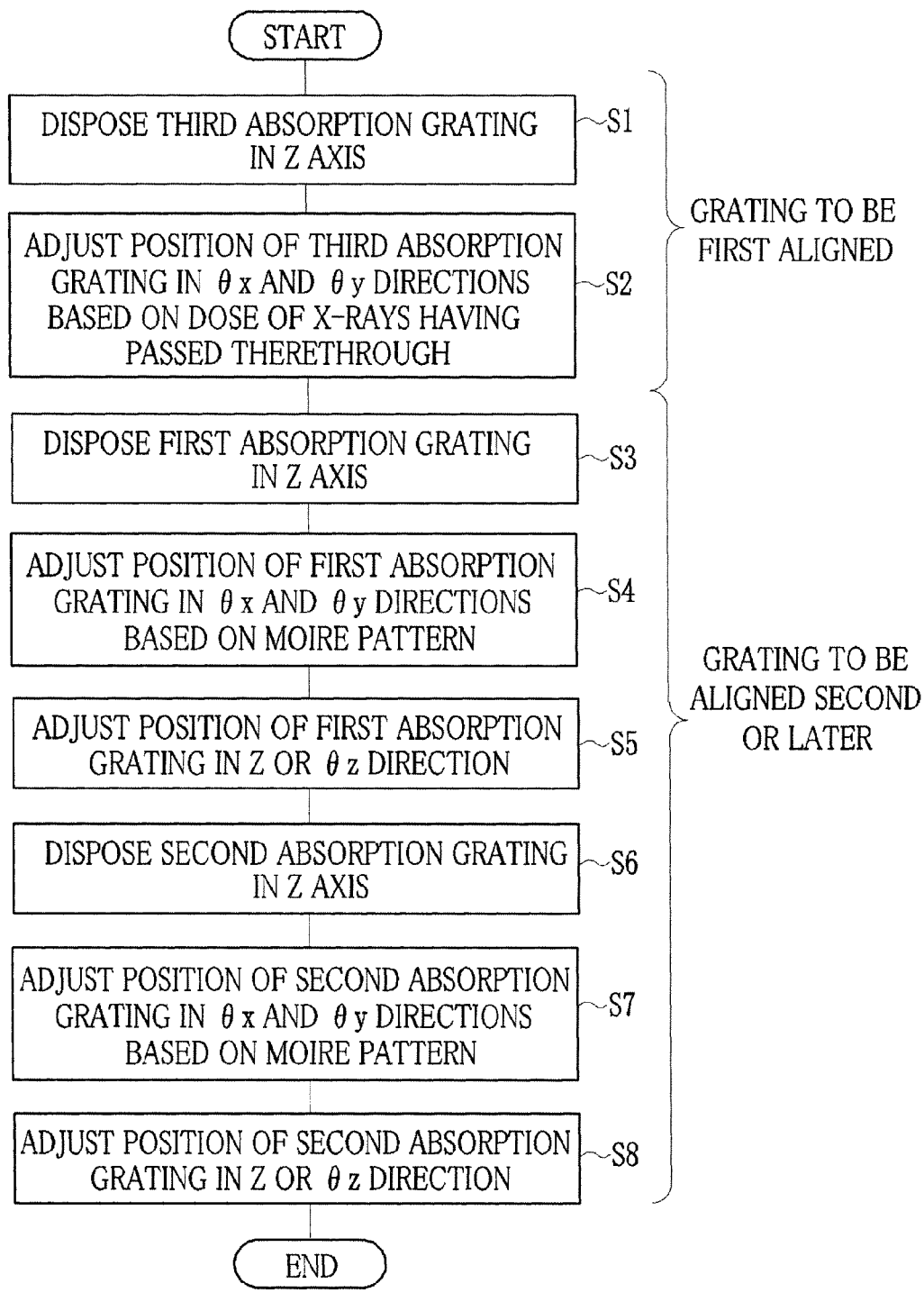

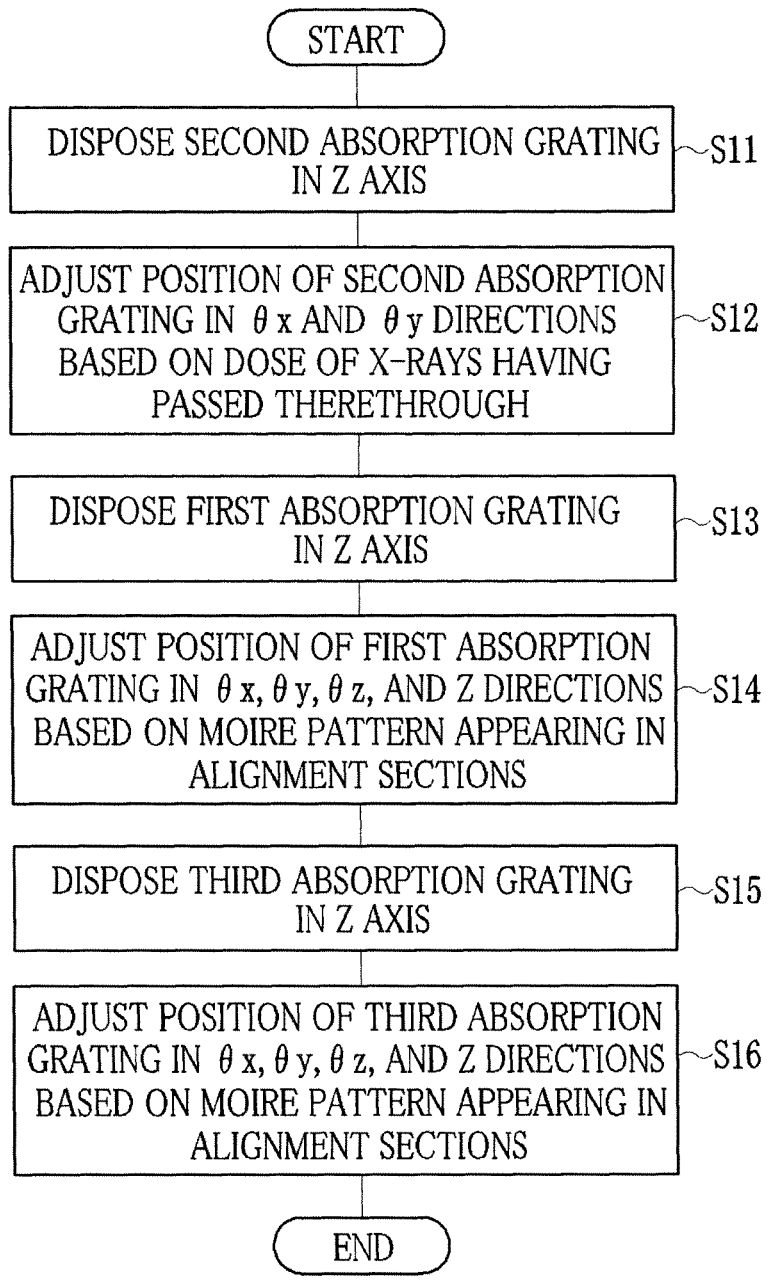

DIFFRACTION GRATING AND ALIGNMENT METHOD THEREOF, AND RADIATION IMAGING SYSTEM

BACKGROUND OF THE INVENTION

1. Field of the Invention

The present invention relates to an alignment method of plural diffraction gratings, and the diffraction gratings that are easy to align, in a radiation imaging system for capturing a phase contrast image of an object with use of the diffraction gratings.

2. Description Related to the Prior Art

X-rays are used as a probe for imaging inside of an object without incision, due to the characteristic that attenuation of the X-rays depends on the atomic number of an element constituting the object and the density and thickness of the object. Radiography using the X-rays is widely available in fields of medical diagnosis, nondestructive inspection, and the like.

In a conventional X-ray imaging system for capturing a radiographic image of the object, the object to be examined is disposed between an X-ray source for emitting the X-rays and an X-ray image detector for detecting the X-rays. The X-rays emitted from the X-ray source are attenuated (absorbed) in accordance with the characteristics (atomic number, density, and thickness) of material of the object present in an X-ray path, and are then incident upon pixels of the X-ray image detector. Thus, the X-ray image detector detects an X-ray absorption image of the object. There are some types of X-ray image detectors in widespread use, such as a combination of an X-ray intensifying screen and a film, an imaging plate containing photostimulated phosphor, and a flat panel detector (FPD) that takes advantage of semiconductor circuits.

The smaller the atomic number of the element constituted of the material, the lower X-ray absorptivity the material has. Thus, the X-ray absorption image of living soft tissue, soft material, or the like cannot have sufficient contrast. Taking a case of an arthrosis of a human body as an example, both of cartilage and joint fluid surrounding the cartilage have water as a predominant ingredient, and little difference in the X-ray absorptivity therebetween. Thus, the X-ray absorption image of the arthrosis hardly has sufficient contrast.

With this problem as a backdrop, X-ray phase imaging is actively researched in recent years. In the X-ray phase imaging, an image (hereinafter called phase contrast image) is obtained based on phase shifts (shifts in angle) of the X-rays that have passed through the object, instead of intensity distribution of the X-rays having passed therethrough. It is generally known that when the X-rays are incident upon the object, the phases of the X-rays interact with the material more closely than the intensity of the X-rays. Accordingly, the X-ray phase imaging, which takes advantage of phase difference, allows obtainment of the image with high contrast, even in capturing the image of the object constituted of the materials that have little difference in the X-ray absorptivity. As a type of such X-ray phase imaging, is proposed an X-ray imaging system using an X-ray Talbot interferometer, which is constituted of two transmission diffraction gratings and the X-ray image detector (refer to Japanese Patent Laid-Open Publication No. 2008-200359 and Applied Physics Letters, Vol. 81, No. 17, page 3287, written on October 2002 by C. David et al., for example).

The X-ray Talbot interferometer is constituted of the X-ray source, the X-ray image detector, and first and second diffraction gratings disposed between the X-ray source and the X-ray image detector. The first diffraction grating is disposed behind the object. The second diffraction grating is disposed downstream from the first diffraction grating by a specific distance (Talbot distance), which is determined from a grating pitch of the first diffraction grating and the wavelength of the X-rays. The Talbot distance is a distance at which the X-rays that have passed through the first diffraction grating form a self image by the Talbot effect. If the object is disposed between the X-ray source and the first diffraction grating or between the first diffraction grating and a self image observation position (in this case, the Talbot distance), this self image is spatially modulated according to the interaction (phase shifts) between the X-rays and the object.

In the X-ray Talbot interferometer, the second diffraction grating is overlaid on the self image of the first diffraction grating to obtain a fringe image subjected to intensity modulation. The fringe image is detected by a fringe scanning technique. From variation (phase shift) of the fringe image due to the presence of the object, an intensity contrast image of the object is obtained. In the fringe scanning technique, a plurality of images are captured, while the second diffraction grating is slid relatively against the first diffraction grating in a direction substantially parallel to a surface of the first diffraction grating and substantially orthogonal to a grating direction of the first diffraction grating at a scan pitch that corresponds with an equally divided part of a grating pitch. By this scanning operation, is obtained series data (hereinafter called intensity modulation signal) composed of pixel data the intensity of which is periodically changed on a pixel basis of the X-ray image detector. From a phase shift amount (a phase shift amount between the presence and the absence of the object) of this intensity modulation signal, a differential phase image (corresponding to angular distribution of the X-rays refracted by the object) is obtained. Furthermore, integration of the differential phase image along a fringe scanning direction allows obtainment of the phase contrast image. This fringe scanning technique is also adopted in an imaging system using laser light (refer to Applied Optics, Vol. 37, No. 26, page 6227, written on September 1998 by Hector Canabal et al.).

If the focus size of the X-ray source is large, the self image of the first diffraction grating is blurred, and the blur causes degradation in image quality of the phase contrast image. To prevent this problem, is known an X-ray imaging system having a third diffraction grating (source grating) disposed just behind the X-ray source. The third diffraction grating partly blocks the X-rays emitted from the X-ray source to reduce the effective focus size, and forms a number of narrow point sources (distributed light sources), in order to prevent the blur of the self image.

To capture the phase contrast image of high image quality, it is necessary to precisely align the X-ray source, the first to third diffraction gratings, and the X-ray image detector. Especially, it is expected that a relative rotation angle among the first to third diffraction gratings is difficult to adjust because slight deviation in the relative rotation angle severely affects the image quality of the phase contrast image. In the X-ray imaging system used in a laboratory, the precise alignment is carried out through use of a measuring instrument with high degree of accuracy. However, in the commercial X-ray imaging system set up in a hospital or the like, the use of the highly accurate measuring instrument is out of reality, and the establishment of any alignment technique is desired.

SUMMARY OF THE INVENTION

An object of the present invention is to provide a method for adjusting the position and angle of plural diffraction gratings without use of a measuring instrument having high degree of accuracy, and the diffraction grating convenient for the adjustment in a radiation imaging system for capturing a phase contrast image with use of the diffraction gratings.

To achieve the above and other objects of the present invention, an alignment method of plural diffraction gratings according to the present invention includes the steps of disposing one of the plural diffraction gratings to be first aligned in a Z axis orthogonal to a detection surface of the radiation image detector; after the disposition of the diffraction grating to be first aligned, while the diffraction grating to be first aligned is rotated in a θx direction about an X axis orthogonal to the Z axis and in a θy direction about a Y axis orthogonal to the Z and X axes, measuring a dose of the radiation having passed through the diffraction grating to be first aligned, and locating the diffraction grating to be first aligned in such a position in the θx and θy directions that the dose of the radiation is maximized; after the location of the diffraction grating to be first aligned, disposing in the Z axis another one of the plural diffraction gratings to be aligned second or later, so that the radiation forms a moiré pattern; after the disposition of the diffraction grating to be aligned second or later, while the diffraction grating to be aligned second or later is rotated in the θx and θy directions, detecting the moiré pattern by the radiation image detector, and locating the diffraction grating to be aligned second or later in such a position in the θx and θy directions that a frequency of the moiré pattern becomes uniform; and adjusting at least one of a relative position among the plural diffraction gratings along a direction of the Z axis and a relative position among the plural diffraction gratings in a θz direction about the Z axis, so that the radiation image detector loses the detection of the moiré pattern.

In the adjustment step, at least one of the relative position among the plural diffraction gratings along the direction of the Z axis and the relative position among the plural diffraction gratings in the θz direction may be adjusted, so that a period of the moiré pattern becomes larger than a detection area of the radiation image detector.

It is preferable that the plural diffraction gratings include a first diffraction grating for passing the radiation and producing a fringe image, and a second diffraction grating for applying intensity modulation to the fringe image in each of plural relative positions out of phase with one another with respect to a periodic pattern of the fringe image.

The plural diffraction gratings may further include a third diffraction grating disposed between the radiation source and the first diffraction grating. The third diffraction grating partly blocks the radiation emitted from the radiation source and produces plural line sources. The third diffraction grating is to be aligned first or second.

In the disposition step of the diffraction grating to be aligned second or later, the diffraction grating to be aligned second or later may be disposed so as to deviate from a target position in the direction of the Z axis or in the θz direction.

A diffraction grating according to the present invention includes plural radiation shield members arranged in one direction, and an alignment section. Each of the radiation shield members extends in a direction orthogonal to the arrangement direction. The plural radiation shield members form a grating pattern. The alignment section includes a grid pattern different from the grating pattern.

The alignment section may have a grid pitch different from a grating pitch of the grating pattern. Otherwise, the grid pattern of the alignment section may be inclined relative to the grating pattern.

The alignment section may include a first alignment pattern having the grid pitch smaller than the grating pitch, and a second alignment pattern having the grid pitch larger than the grating pitch. The alignment section may include a third alignment pattern rotated in a first direction about an axis orthogonal to a grating surface of the diffraction grating, and a fourth alignment pattern rotated in a second direction opposite to the first direction. Furthermore, the alignment section may include a fifth alignment pattern having the grid pattern same as the grating pattern.

The alignment section may be disposed on at least one of four corners of the diffraction grating of a rectangular shape.

A radiation imaging system according to the present invention includes a radiation source for emitting a radiation, a radiation image detector for detecting an image carried on the radiation, and plural diffraction gratings disposed between the radiation source and the radiation image detector. Each of the diffraction gratings includes plural radiation shield members arranged in one direction. Each of the radiation shield members extends in a direction orthogonal to the arrangement direction, and the plural radiation shield members form a grating pattern in each of the diffraction gratings. At least one of the diffraction gratings includes an alignment section including a grid pattern different from the grating pattern. The radiation image detector detects a moiré pattern produced by passage of the radiation through the grating pattern of the diffraction grating without having the alignment section and through the grid pattern of the alignment section, and a relative position among the plural diffraction gratings is adjusted based on the moiré pattern.

According to the present invention, the position and angle of the plural diffraction gratings can be precisely adjusted based on the dose of the passing X-rays and the moiré pattern, which are measurable without use of a measuring instrument with high degree of accuracy, and hence it is possible to obtain the phase contrast image of high image quality. Besides, by providing the alignment section in the diffraction grating to check a state and direction of positional deviation, the position and angle of the plural diffraction gratings are precisely adjustable.

BRIEF DESCRIPTION OF THE DRAWINGS

For more complete understanding of the present invention, and the advantage thereof, reference is now made to the following descriptions taken in conjunction with the accompanying drawings, in which:

FIG. 5 is a flowchart of an alignment procedure of the first absorption grating and second and third absorption gratings;

FIG. 17 is a flowchart of the alignment procedure of the first to third absorption gratings according to the second embodiment.

DESCRIPTION OF THE PREFERRED EMBODIMENTS

First Embodiment

Figure 1:
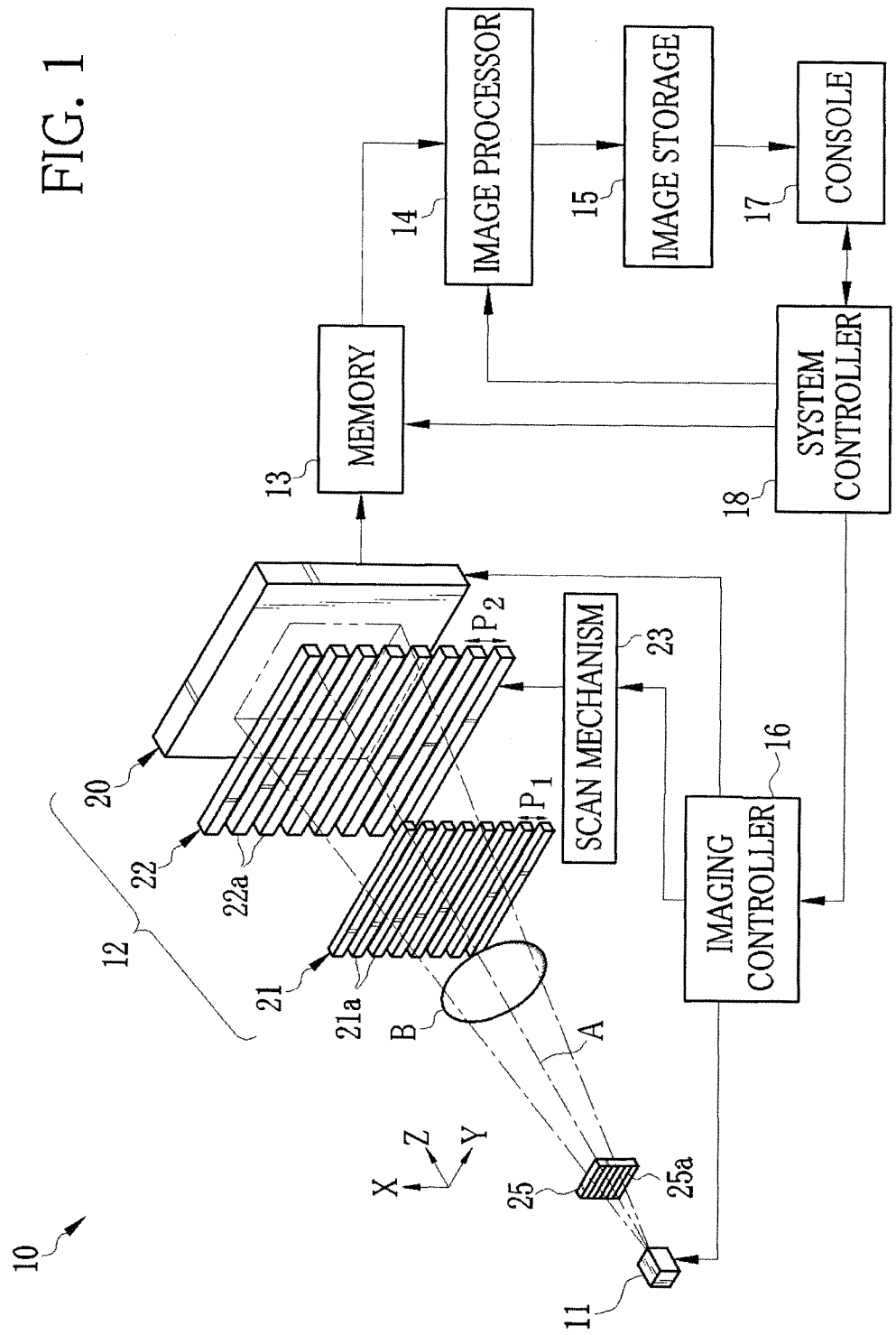
FIG. 1 is a schematic view of an X-ray imaging system according to a first embodiment.

As shown in FIG. 1, an X-ray imaging system 10 according to a first embodiment is constituted of an X-ray source 11 for applying X-rays to an object B, an imaging unit 12 disposed so as to face the X-ray source 11, a memory 13, an image processor 14, an image storage 15, an imaging controller 16, a console 17 including an operation unit and a monitor, and a system controller 18. The imaging unit 12 detects the X-rays that have been emitted from the X-ray source 11 and passed through the object B, to produce image data. The memory 13 stores the image data outputted from the imaging unit 12. The image processor 14 produces a phase contrast image from plural frames of image data stored on the memory 13. The image storage 15 stores the phase contrast image produced by the image processor 14. The imaging controller 16 controls the X-ray source 11 and the imaging unit 12. The system controller 18 carries out centralized control of the entire X-ray imaging system 10 based on an operation signal inputted from the console 17.

The X-ray source 11 is constituted of a high voltage generator, an X-ray tube, a collimator (all of them are not illustrated), and the like, and applies the X-rays to the object B under control of the imaging controller 16. The X-ray tube is, for example, a rotating anode X-ray tube. In the X-ray tube, an electron beam is emitted from a filament in accordance with a voltage generated by the high voltage generator, and collides with an anode rotating at a predetermined speed to generate the X-rays. The anode rotates for the purpose of reducing deterioration caused that the electron beam keeps colliding with a fixed position of the anode. A collision portion by the electron beam is referred to as an X-ray focus from which the X-rays radiate. The collimator restricts an irradiation field of the X-rays emitted from the X-ray tube, so as to block part of the X-rays outside an examination region of the object B.

The imaging unit 12 includes a flat panel detector (FPD) 20 having semiconductor circuits, and first and second absorption gratings 21 and 22 that detect phase shifts (shifts in angle) of the X-rays by the object B for phase imaging. The FPD 20 is disposed in such a position that a detection plane intersects at right angles with a direction (hereinafter called Z direction) along an optical axis A of the X-rays emitted from the X-ray source 11.

In the first absorption grating 21, a plurality of X-ray shield members 21a extending in a direction (hereinafter called Y direction) defined in a plane orthogonal to the Z direction are arranged in a direction (hereinafter called X direction) orthogonal to the Z and Y directions at a predetermined grating pitch $P_1$. In the second absorption grating 22, in a like manner, a plurality of X-ray shield members 22a extending in the Y direction are arranged in the X direction at a predetermined grating pitch $P_2$. The X-ray shield members 21a and 22a are preferably made of metal having high X-ray absorptivity, such as gold, platinum, lead, and tungsten.

The imaging unit 12 is provided with a scan mechanism 23 that slides the second absorption grating 22 in a direction (X direction) orthogonal to a grating direction to vary the relative position between the first and second absorption gratings 21 and 22. The scan mechanism 23 is constituted of an actuator such as a piezoelectric element, for example. The scan mechanism 23 is driven under the control of the imaging controller 16 during fringe scanning described later on. Although details will be described later on, the memory 13 stores the image data obtained in each scan step of the fringe scanning by the imaging unit 12. The second absorption grating 22 and the scan mechanism 23 compose an intensity modulator.

A third absorption grating 25 is disposed between the X-ray source 11 and the first absorption grating 21, and just behind the X-ray source 11. The third absorption grating 25 is geometrically similar to the first and second absorption gratings 21 and 22 provided in the imaging unit 12. In the third absorption grating 25, a plurality of X-ray shield members 25a extending in one direction (Y direction in this embodiment) are periodically arranged in the same direction (X direction in this embodiment) as that of the X-ray shield members 21a and 22a of the first and second absorption gratings 21 and 22.

The third absorption grating 25 partly blocks the X-rays emitted from the X-ray source 11 by the X-ray shield members 25a, to reduce an effective focus size in the X direction and form a number of point sources (distributed light sources) in the X direction. Thus, the reduction in the effective focus size of the X-ray source 11 allows prevention of a blur occurring in a self image of the first absorption grating 21. The third absorption grating 25 may be integrated into the X-ray source 11.

The image processor 14 produces a differential phase image from the plural frames of image data, which are captured in each scan step of the fringe scanning by the imaging unit 12 and stored on the memory 13. Then, the image processor 14 produces the phase contrast image by integration of the differential phase image along the X direction. The phase contrast image is written to the image storage 15, and then is outputted to the console 17 for display on a monitor (not illustrated).

The console 17 is provided with an input device (not illustrated) on which an imaging command and command contents are inputted, in addition to the monitor. The input device includes, for example, a switch, a touch panel, a mouse, and a key board. Operation on the input device allows input of X-ray imaging conditions such as the voltage of the X-ray tube and X-ray irradiation time, imaging timing, and the like. The monitor is a liquid crystal display or a CRT display, and displays text of the X-ray imaging conditions and the above phase contrast image.

Figure 2:
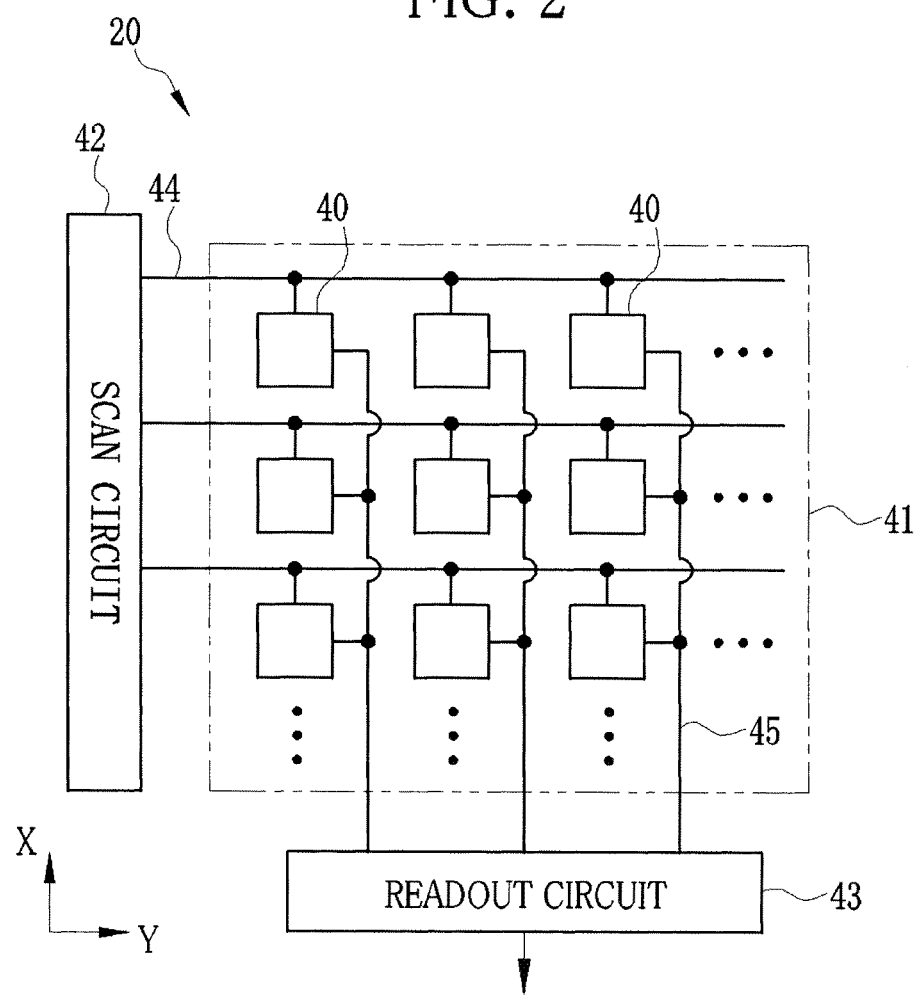
FIG. 2 is a schematic view of a flat panel detector.

As shown in FIG. 2, the FPD 20 is constituted of an imaging section 41, a scan circuit 42, and a readout circuit 43. The imaging section 41 has a plurality of pixels 40 arranged in two dimensions along the X and Y directions on an active matrix substrate. Each of the pixels 40 converts the X-rays into an electric charge and accumulates the electric charge. The scan circuit 42 controls readout timing of the electric charges from the imaging section 41. The readout circuit 43 reads out the electric charge accumulated in each pixel 40. Then, the readout circuit 43 converts the electric charges into the image data, and writes the image data to the memory 13. The scan circuit 42 is connected to every pixel 40 by scan lines 44 on a row basis. The readout circuit 43 is connected to every pixel 40 by signal lines 45 on a column basis. The pixels 40 are arranged at a pitch of approximately 100 µm in each of the X and Y directions.

Each pixel 40 is a direct conversion type X-ray detecting element, in which a conversion layer (not illustrated) made of amorphous selenium or the like directly converts the X-rays into the electric charge, and the converted electric charge is accumulated in a capacitor (not illustrated) that is connected to an electrode below the conversion layer. To each pixel 40, a TFT switch (not illustrated) is connected. To be more specific, a gate electrode of the TFT switch is connected to the scan line 44, and a source electrode thereof is connected to the capacitor, and a drain electrode thereof is connected to the signal line 45. Upon turning on the TFT switch by a drive pulse from the scan circuit 42, the electric charge accumulated in the capacitor is read out to the signal line 45.

Each pixel 40 may be an indirect conversion type X-ray detecting element, in which a scintillator (not illustrated) made of gadolinium oxide ($Gd_2O_3$), cesium iodide (CsI), or the like converts the X-rays into visible light, and a photodiode (not illustrated) converts the visible light into the electric charge. In this embodiment, the FPD based on a TFT panel is used as a radiation image detector, but various types of radiation image detectors based on a solid-state image sensor such as a CCD image sensor and a CMOS image sensor may be used instead.

The readout circuit 43 includes an integration amplifier, an A/D converter, and a correction section (none of them is illustrated), and the like. The integration amplifier integrates the electric charge outputted from each pixel 40 through the signal line 45, to convert the electric charge into a voltage signal (image signal). The A/D converter converts the image signal produced by the integration amplifier into digital image data. The correction section applies offset correct, gain correction, linearity correction, and the like to the image data, and writes the corrected image data to the memory 13.

Figure 3:
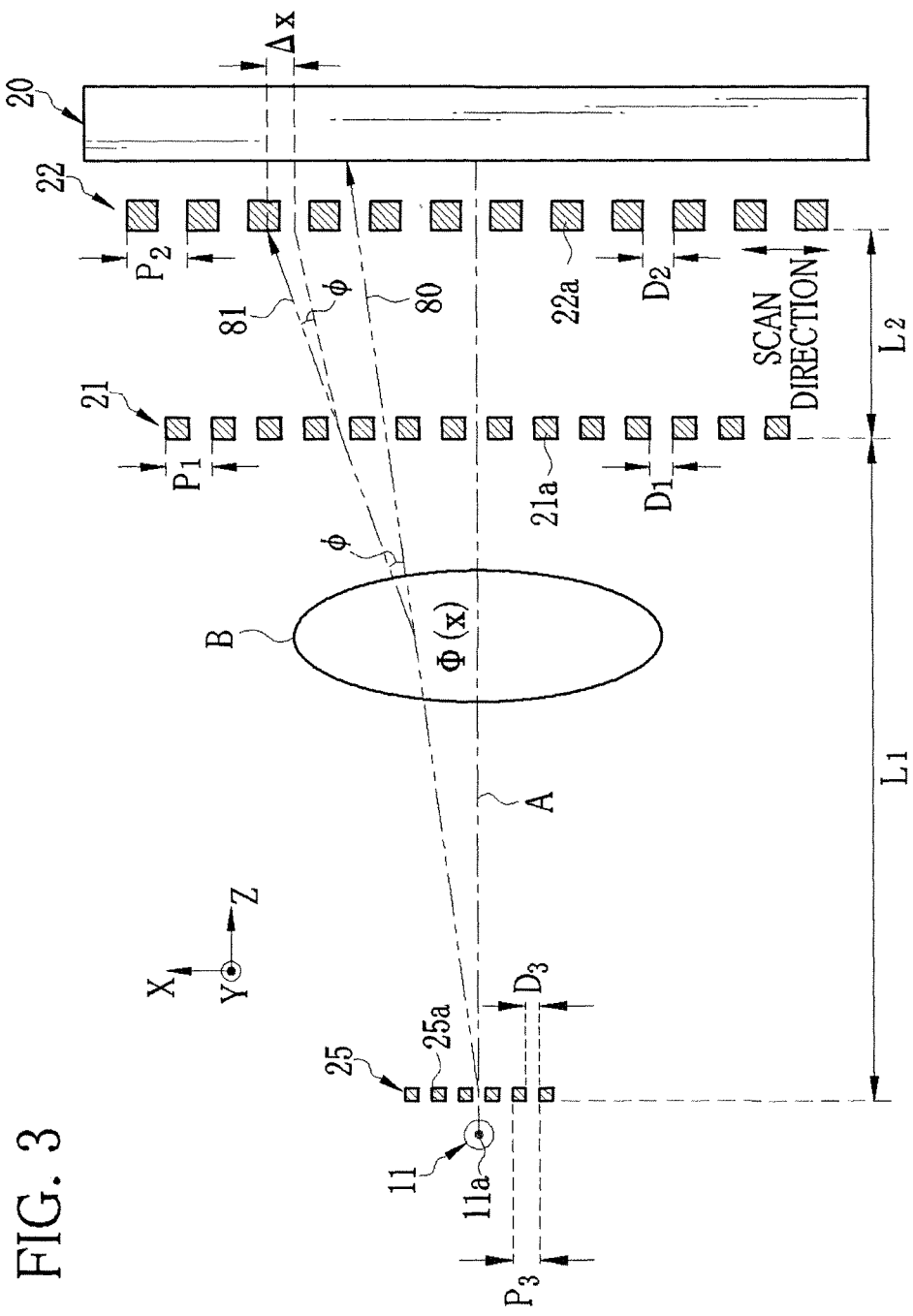
FIG. 3 is a schematic side view of an X-ray source, an object, and an imaging unit, and shows an example of difference in an X-ray path between the presence and the absence of the object.

In FIG. 3, the X-ray shield members 21a of the first absorption grating 21 are arranged in the X direction at the predetermined grating pitch $P_1$ and at a predetermined spacing distance $D_1$ apart from one another. The X-ray shield members 22a of the second absorption grating 22 are arranged in the X direction at the predetermined grating pitch $P_2$ and at a predetermined spacing distance $D_2$ apart from one another. Also, the X-ray shield members 25a of the third absorption grating 25 are arranged in the X direction at a predetermined grating pitch $P_3$ and at a predetermined spacing distance $D_3$ apart from one another. The X-ray shield members 21a, 22a, and 25a are arranged on not-illustrated X-ray transparent substrates (for example, glass substrates) to form each individual grating. The first and third absorption gratings 21, 22, and 25 provide the incident X-rays not with phase difference but with intensity difference. Thus, the first and third absorption gratings 21, 22, and 25 are referred to as amplitude gratings. Slits (regions of the spacing distances $D_1$, $D_2$, and $D_3$) may not be clearances, but may be filled with an X-ray low-absorbent material such as a high polymer and light metal.

Irrespective of the presence or absence of the Talbot effect, the first and second absorption gratings 21 and 22 are designed so as to linearly project the X-rays having passed through the slits. To be more specific, the spacing distances $D_1$ and $D_2$ are set sufficiently larger than a peak wavelength of the X-rays emitted from the X-ray source 11, so that the X-rays applied to the slits are not diffracted but pass therethrough straight ahead. In a case where tungsten is used as the rotating anode of the X-ray tube and the voltage of the X-ray tube is 50 kV, for example, the peak wavelength of the X-rays is approximately 0.4 Å. In this case, if the spacing distances $D_1$ and $D_2$ are set at the order of 1 to 10 µm, almost all of the X-rays are linearly projected through the slits without diffraction. In this case, the grating pitches $P_1$ and $P_2$ are set at the order of 2 to 20 µm.

The X-rays emitted from the X-ray source 11 do not form a parallel beam, but form a cone beam radiating from the X-ray focus. Thus, a projective image (hereinafter called G1 image or fringe image) projected through the first absorption grating 21 is magnified in proportion to a distance from the third absorption grating 25, which substantially becomes the X-ray focus. The grating pitch $P_2$ and spacing distance $D_2$ of the second absorption grating 22 are designed so that the slits of the second absorption grating 22 substantially coincide with a periodic pattern of bright portions of the G1 image formed in the position of the second grating 22. In other words, the grating pitch $P_2$ and spacing distance $D_2$ of the second absorption grating 22 satisfy the following expressions (1) and (2):

$$P_2 = \frac{L_1 + L_2}{L_1} P_1 \qquad (1)$$

$$D_2 = \frac{L_1 + L_2}{L_1} D_1 \qquad (2)$$

Wherein, $L_1$ represents a length from the third absorption grating 25 to the first absorption grating 21, and $L_2$ represents a length from the first absorption grating 21 to the second absorption grating 22.

Also, the grating pitch $P_3$ of the third absorption grating 25 satisfies the following expressions (3):

$$P_3 = \frac{L_1}{L_2} P_2 \qquad (3)$$

In the case of the Talbot interferometer, the length $L_2$ between the first and second absorption gratings 21 and 22 is restricted to a Talbot distance, which depends on the grating pitch of the first diffraction grating and the wavelength of the X-rays. According to the imaging unit 12 of this embodiment, however, since the incident X-rays are projected through the first absorption grating 21 without diffraction, the G1 image of the first absorption grating 21 is observable in any position behind the first absorption grating 21 in a geometrically similar manner. Thus, the length $L_2$ can be established irrespective of the Talbot distance.

Although the imaging unit 12 according to this embodiment does not compose the Talbot interferometer, as described above, the Talbot distance Z is represented by the following expression (4), on the assumption that the first absorption grating 21 diffracts the X-rays and produces the Talbot effect:

$$Z = m \frac{P_1 P_2}{\lambda} \quad (4)$$

Wherein, λ represents the wavelength (peak wavelength) of the X-rays, and m represents a positive integer.

The expression (4) represents the Talbot distance when the X-rays emitted from the X-ray source 11 form the cone beam, and is known by Japanese Journal of Applied Physics, Vol. 47, No. 10, page 8077, written on October 2008 by Atsushi Momose et al.

In this embodiment, since the length $L_2$ can be established irrespective of the Talbot distance, as described above, the length $L_2$ is set shorter than the minimum Talbot distance Z defined at m=1, for the purpose of downsizing the imaging unit 12 in the Z direction. In other words, the length $L_2$ satisfies the following expression (5):

$$L_2 < \frac{P_1 P_2}{\lambda} \quad (5)$$

To produce a periodic pattern image with high contrast, it is preferable that the X-ray shield members 21a, 22a, and 25a completely block (absorb) the X-rays. However, some of the X-rays pass through the X-ray shield members 21a, 22a, and 25a without being absorbed, even with the use of the above material having high X-ray absorptivity (gold, platinum, lead, tungsten, or the like). For this reason, it is preferable to thicken each of the X-ray shield members 21a, 22a, and 25a (thickness in the Z direction) as much as possible (in other words, increase an aspect ratio of each shield member 21a, 22a, and 25a), to increase X-ray shielding ability. For example, when the voltage of the X-ray tube is 50 kV, it is preferable to block 90% or more of the applied X-rays. In this case, the thickness of each X-ray shield member 21a, 22a, 25a is preferably 30 μm or more on a gold (Au) basis.

With use of the first and second absorption gratings 21 and 22 having above structure, the FPD 20 captures a fringe image subjected to intensity modulation by superimposing the second absorption grating 22 on the G1 image (fringe image) of the first absorption grating 21. A pattern period of the G1 image formed in the position of the second absorption grating 22 is slightly different from the grating pitch $P_2$ of the second absorption grating 22 due to a manufacturing error and a placement error. This slight difference causes moiré fringes occurring in the fringe image subjected to the intensity modulation. If an error occurs between the grating directions of the first and second absorption gratings 21 and 22, and the grating directions are different from each other, a so-called rotation moiré appears. However, the moiré fringes appearing in the fringe image do not cause any problem if the periods of the moiré fringes in the X and Y directions are larger than the arrangement pitch of the pixels 40. The nonexistence of the moiré fringes is ideal, but the moiré fringes are available for checking a scan distance (sliding distance of the second absorption grating 22) of the fringe scanning, as described later on.

If the object B is disposed between the X-ray source 11 and the first absorption grating 21, the fringe image detected by the FPD 20 is modulated by the object B. This modulation amount is proportional to deviation angles of the X-rays due to a refraction effect by the object B. Consequently, analysis of the fringe image detected by the FPD 20 allows production of the phase contrast image of the object B.

Figure 4A:
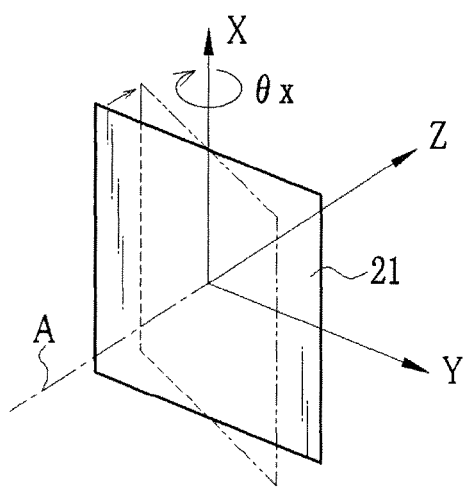
FIGS. 4A to 4C are explanatory views that explain directions of a rotational deviation of a first absorption grating.
Figure 4B:
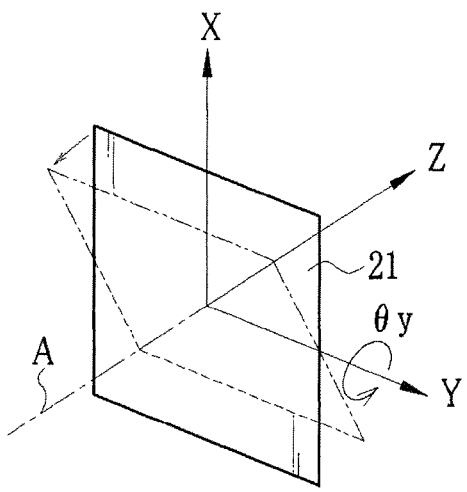
Figure 4C:
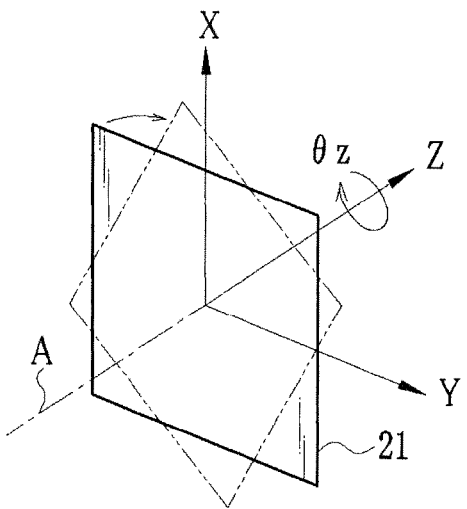

Next, an alignment method of the first to third absorption gratings 21, 22, and 25 will be described. To appropriately capture the phase contrast image by the X-ray imaging system 10, the first to third absorption gratings 21, 22, and 25 have to satisfy the above expressions (1) and (3). Also, grating surfaces of the first to third absorption gratings 21, 22, and 25 have to be in parallel with an X-Y plane, and the rotation positions of the first to third absorption gratings 21, 22, and 25 about the optical axis A coincide with one another. At this time, the deviations among the first to third absorption gratings 21, 22, and 25 in the X and Y directions do not affect the phase contrast image, and hence present no problem as long as the first to third absorption gratings 21, 22, and 25 are roughly aligned in those directions. On the contrary, the first to third absorption gratings 21, 22, and 25 are to be precisely aligned in a position of the Z direction, and in rotation angles of θx, θy, and θz directions shown in FIGS. 4A to 4C.

As shown in a flowchart of FIG. 5, how to align a grating to be first aligned is different from that of a grating to be aligned second or later, in this embodiment. In a case where the third absorption grating 25 is firstly aligned, for example, the third absorption grating 25 is disposed in an appropriate position between the X-ray source 11 and the FPD 20 in a Z axis (S1). Then, the position of the third absorption grating 25 is adjusted in the θx and θy directions (S2). The adjustment of the position in the θx and θy directions is carried out by measuring a dose of the X-rays that have passed through the third absorption grating 25, while the third absorption grating 25 is rotated in the θx and θy directions.

Figure 6A:
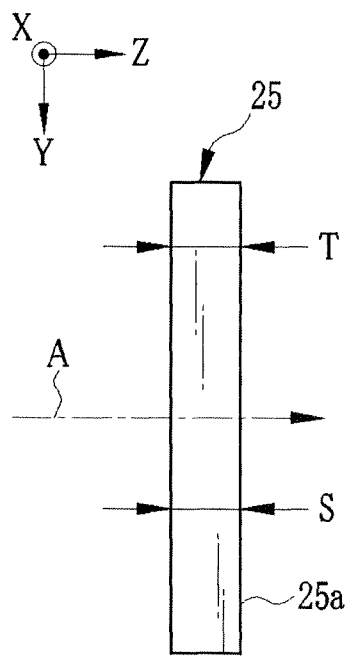
FIGS. 6A and 6B are explanatory views that explain a variation of X-ray transmittance caused by a deviation of the third absorption grating in a θx direction.
Figure 6B:
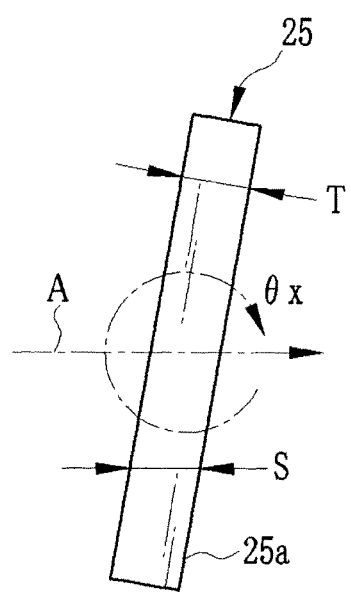
Figure 7A:
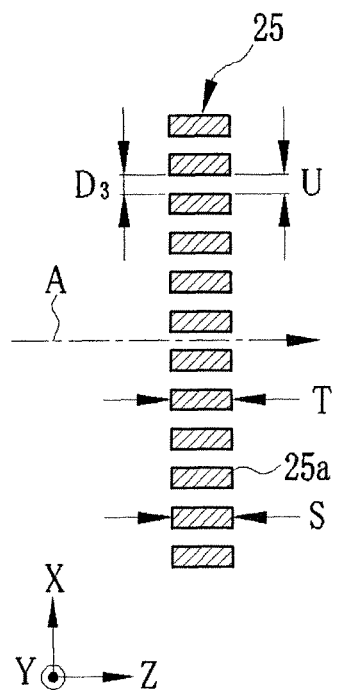
FIGS. 7A and 7B are explanatory views that explain a variation of the X-ray transmittance caused by a deviation of the third absorption grating in a θy direction.
Figure 7B:
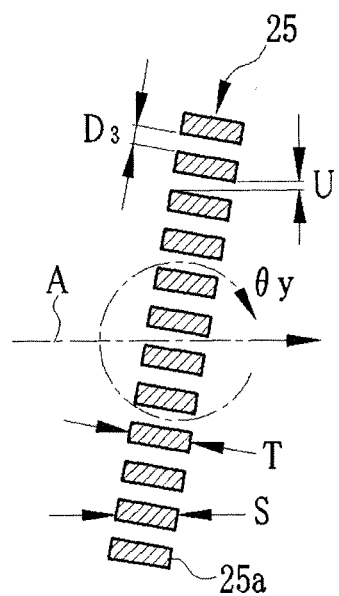

As shown in FIGS. 6A and 7A, if the grating surface of the third absorption grating 25 is in parallel with the X-Y plane, a passing distance S of the X-rays passing through the X-ray shield member 25a is equal to a thickness T of the X-ray shield member 25a, and the width of a clearance U between the X-ray shield members 25a along the optical axis A is equal to the spacing distance $D_3$. On the other hand, if the grating surface of the third absorption grating 25 is not in parallel with the X-Y plane, as shown in FIGS. 6B and 7B, the passing distance S becomes larger than the thickness T, and the width of the clearance U becomes narrower than the spacing distance $D_3$. Thus, apparent X-ray transmittance of the third absorption grating 25 is reduced. For this reason, by finding the position in the θx and θy directions where the dose of the X-rays having passed through the third absorption grating 25 is maximized, the grating surface of the third absorption grating 25 is set in parallel with the X-Y plane. To measure the dose of the X-rays, either of an X-ray dosimeter and the FPD 20 is available.

The alignment of the grating to be aligned second or later uses the moiré pattern that appears by the passage of the X-rays through the plural gratings. This is because in a case where the plural gratings are in optimal positions relative to each other, the dose of the X-rays that reach the FPD 20 can be an arbitrary value from maximum to minimum according to the positional relation in the X direction, and hence the position of the grating to be aligned second or later cannot be determined by dose information.

For example, if the first absorption grating 21 is chosen as the grating to be second aligned, the first absorption grating 21 is disposed in an appropriate position between the third absorption grating 25 and the FPD 20 in the Z direction (S3). At this time, the first absorption grating 21 is disposed so as to intentionally deviate in the Z or θz direction, for the purpose of producing the moiré pattern by the X-rays that have passed through the first and third absorption gratings 21 and 25.

Figure 8A:
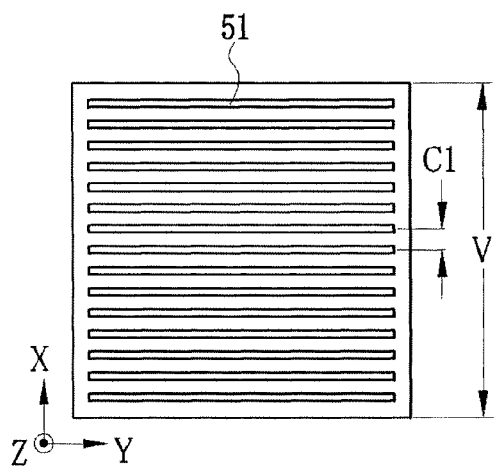
FIGS. 8A to 8D are explanatory views showing variations in a moiré pattern caused by a deviation of the second absorption grating.
Figure 8B:
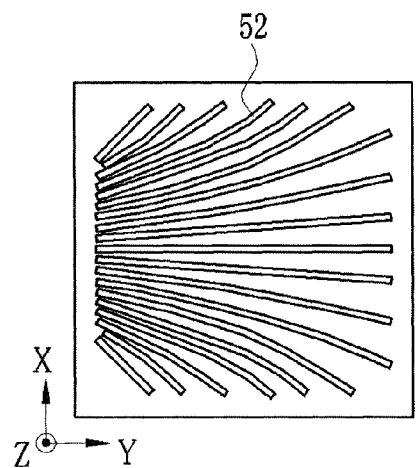

Then, the position of the first absorption grating 21 is adjusted in the θx and θy directions based on the moiré pattern detected by the FPD 20 (S4). As shown in FIG. 8A, if the first absorption grating 21 deviates only in the Z direction, a uniform striped moiré pattern 51 having a constant frequency in the X direction is detected. The detection of this moiré pattern 51 eliminates the need for adjusting the position of the first absorption grating 21 in the θx and θy directions.

If the first absorption grating 21 deviates in the θx direction, as shown in FIG. 8A, a radial moiré pattern 52 in which the frequency is constant in the X direction but is varied in the Y direction is detected. If this moiré pattern 52 is detected, the position of the first absorption grating 21 has to be adjusted in the θx direction so as to have the uniform striped moiré pattern 51 as shown in FIG. 8A.

Figure 8C:
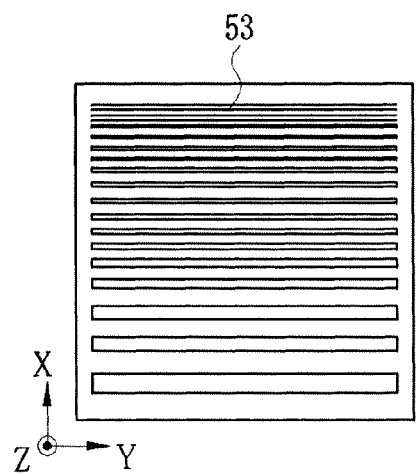

If the first absorption grating 21 deviates in the θy direction, as shown in FIG. 8C, a nonuniform striped moiré pattern 53 having a gradually varied frequency in the X direction is detected. If this moiré pattern 52 is detected, the position of the first absorption grating 21 has to be adjusted in the θy direction so as to have the uniform striped moiré pattern 51 as shown in FIG. 8A.

Figure 8D:
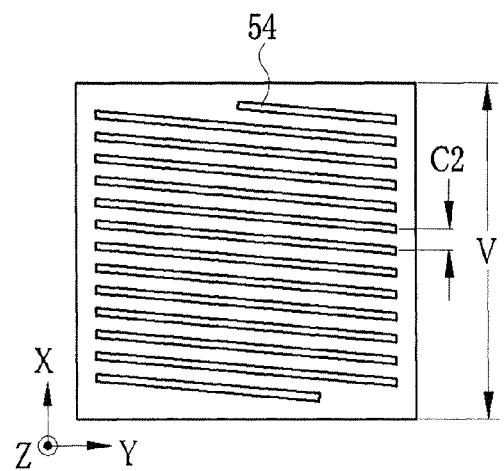

If the first absorption grating 21 deviates in the θz direction in FIG. 8D, a uniform striped and rotated moiré pattern 54 is detected. The detection of this moiré pattern 54 eliminates the need for adjusting the position of the absorption grating 21 in the θx and θy directions.

The first absorption grating 21 does not always deviate in only one of the Z, θx, θy, and θz directions, but may deviate in the plural directions in combination with one another. In such a case, a combined deviation direction of the first absorption grating 21 is analyzed from the detected moiré pattern, and the position of the first absorption grating 21 is adjusted in the θx and θy directions.

Figure 9:
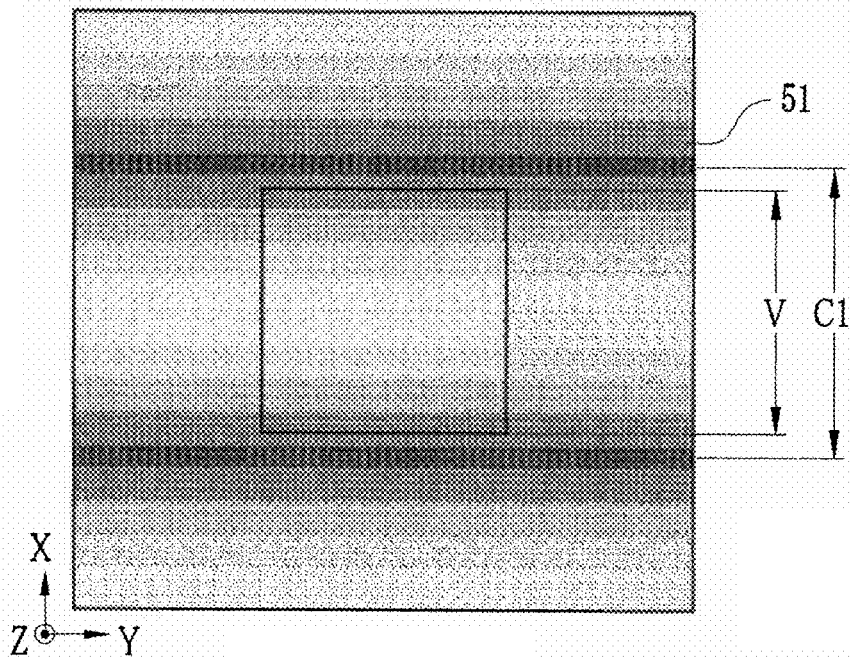
FIG. 9 is an explanatory view of the moiré pattern the period of which is elongated by adjustment of the position of the second absorption grating.

As shown in FIG. 5, the position of the first absorption grating 21 is firstly adjusted in the θx and θy directions, and then adjusted in the Z or θz direction (S5). In this adjustment, the first absorption grating 21 is shifted in the Z direction to vary a period C1 of the moiré pattern 51 in the X direction, or rotated in the θz direction to vary a period C2 of the moiré pattern 54 in the X direction. For example, by setting the period C1 longer than a detection area V of the FPD 20 along the X direction, as shown in FIG. 9, the position of the first absorption grating 21 is determined in the Z or θz direction so that the FPD 20 comes not to detect the moiré pattern 51 or 54.

Therefore, it is possible to prevent the phase contrast image from being affected by the moiré pattern. As shown in FIG. 9, concentration continuously grades in the detection area V of the FPD 20 in accordance with the long period C1 of the moiré pattern 51. However, since the period C1 of the moiré pattern 51 is longer than the detection area V, the moiré pattern 51 is not visually recognized. To avoid the visual recognition of the moiré pattern 51, it is also conceivable to shorten the period C1 of the moiré pattern 51 to a high degree. However, if the period C1 is nearly equal to the arrangement pitch of the FPD 20, the moiré pattern 51 affects the phase contrast image. Thus, it is preferable that the period C1 of the moiré pattern 51 is set longer than the detection area V.

The second absorption grating 22 being the grating to be third aligned is disposed in a like manner as the first absorption grating 21 (S6). Then, the position of the second absorption grating 22 is adjusted in the θx and θy directions (S7), and is adjusted in the Z or θz direction (S8). Since a way to align the second absorption grating 22 is the same as that of the first absorption grating 21, detailed description thereof is omitted.

Next, a method for analyzing the fringe image will be described. FIG. 3 shows an example of the X-ray that is refracted according to phase shift distribution $\Phi(x)$ with respect to the X direction of the object B. A reference numeral 80 indicates a path of the X-ray that travels in a straight line in the absence of the object B. The X-ray traveling in this path 80 passes through the first and second absorption gratings 21 and 22, and is incident upon the FPD 20. A reference numeral 81, on the other hand, indicates a path of the X-ray that is refracted by the object B in the presence of the object B. The X-ray traveling in this path 81 passes through the first absorption grating 21, and then is blocked by the X-ray shield member 22a of the second absorption grating 22.

The phase shift distribution $\Phi(x)$ of the object B is represented by the following expression (6):

$$\Phi(x) = \frac{2\pi}{\lambda} \int [1 - n(x, z)] dz \tag{6}$$

Wherein, $n(x, z)$ represents refractive index distribution of the object B, and z represents a direction in which the X-rays travel. For the sake of simplicity, a Y coordinate is omitted in the expression (6).

The G1 image projected from the first absorption grating 21 to the position of the second absorption grating 22 is displaced in the X direction by an amount based on a refraction angle $\phi$ due to the refraction of the X-ray by the object B. This displacement amount $\Delta x$ by the refraction is approximately represented by the following expression (7), on condition that the refraction angle $\phi$ is sufficiently small:

$$\Delta x \approx L_2 \phi \tag{7}$$

The refraction angle $\phi$ is represented by the following expression (8), with the use of the wavelength $\lambda$ of the X-ray and the phase shift distribution $\Phi(x)$ of the object B:

$$\phi = \frac{\lambda}{2\pi} \frac{\partial \Phi(x)}{\partial x} \tag{8}$$

As is obvious from the above expressions, the displacement amount $\Delta x$ of the G1 image due to the refraction of the X-ray by the object B relates to the phase shift distribution $\Phi(x)$ of the object B. Furthermore, the displacement amount $\Delta x$ relates to a phase shift amount $\psi$ (shift amount in a phase of the intensity modulation signal of each pixel 40 between the presence of the object B and the absence of the object B) of the intensity modulation signal of each pixel 40 detected by the FPD 20, as is represented by the following expression (9):

$$\psi = \frac{2\pi}{P_2} \Delta x = \frac{2\pi}{P_2} L_2 \phi \tag{9}$$

Thus, determination of the phase shift amount $\psi$ of the intensity modulation signal of each pixel 40 leads to obtainment of the refraction angle $\phi$ by using the expression (9), and furthermore leads to obtainment of the differentiation of the phase shift distribution $\Phi(x)$ by using the expression (8). Integrating the differentiation with respect to x allows obtainment of the phase shift distribution $\Phi(x)$ of the object B, that is, production of the phase contrast image of the object B. In this embodiment, the above phase shift amount $\psi$ is determined by a fringe scanning technique described below.

In the fringe scanning technique, the images are captured, while one of the first and second absorption gratings 21 and 22 is slid relatively against the other in a stepwise manner in the X direction. In other words, the image is captured, whenever changing a phase of a grating period of one of the first and second absorption gratings 21 and 22 against that of the other. In this embodiment, the scan mechanism 23 described above slides the second absorption grating 22. With the sliding of the second absorption grating 22, the moiré fringes move. When a sliding distance (sliding amount in the X direction) reaches the single grating period (grating pitch $P_2$) of the second absorption grating 22, in other words, when the phase shift amount reaches $2\pi$, the moiré fringes return to the original positions. The FPD 20 captures the fringe images, while the second absorption grating 22 is slid at a scan pitch of an integer submultiple of the grating pitch $P_2$. Then, the intensity modulation signal of each pixel 40 is obtained from the captured plural fringe images. The image processor 14 applies arithmetic processing to the intensity modulation signal, to obtain the phase shift amount $\psi$ of the intensity modulation signal of each pixel 40. The two-dimensional distribution of the phase shift amounts $\psi$ corresponds to the differential phase image.

Figure 10:
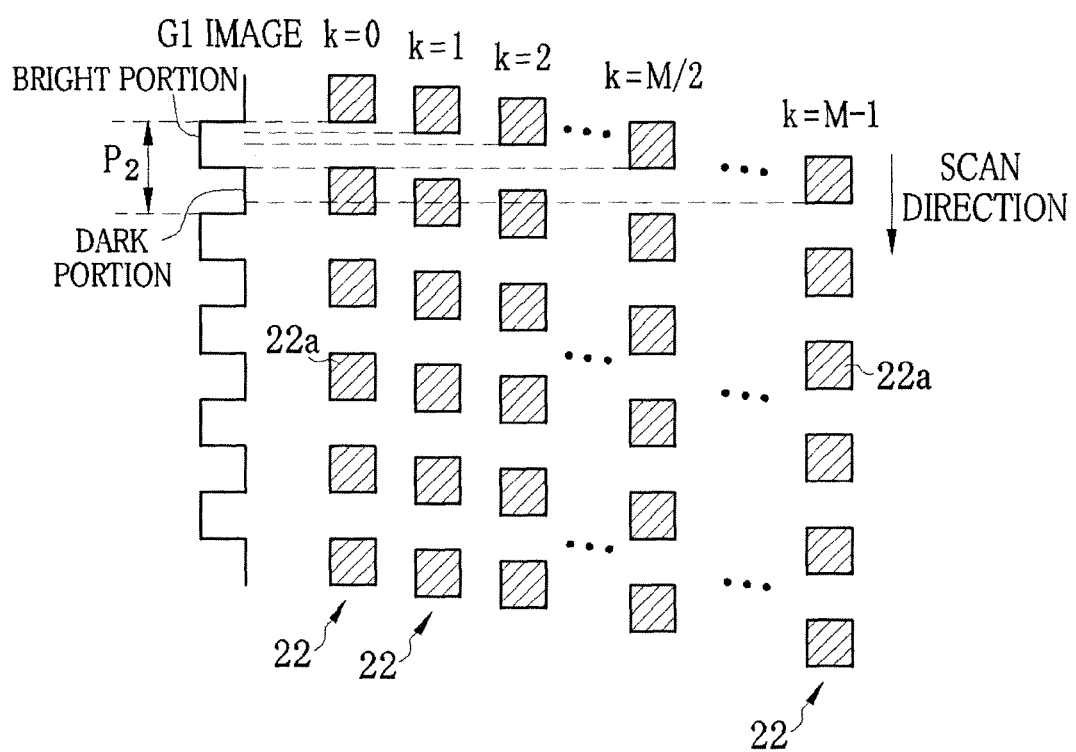
FIG. 10 is an explanatory view of a fringe scanning technique.

FIG. 10 schematically shows a state of shifting the second absorption grating 22 by a scan pitch of $P_2/M$, in which the grating pitch $P_2$ is divided by M (integer of 2 or more). The scan mechanism 23 stepwise slides the second absorption grating 22 to each of an M number of scan positions represented by k=0, 1, 2, ..., M−1. According to FIG. 10, an initial position of the second absorption grating 22 is defined as a position (k=0) in which the X-ray shield members 22a substantially coincide with dark portions of the G1 image formed in the position of the second absorption grating 22 in the absence of the object B. However, the initial position may be defined as any position out of k=0, 1, 2, ... M−1.

In the position of k=0, the X-rays to be detected through the second absorption grating 22 include a component (non-refracted X-ray component) of the X-rays that have not been refracted by the object B, and a part of a component (refracted X-ray component) of the X-rays that have been refracted by the object B and passed through the first absorption grating 21. While the second absorption grating 22 is successively slid to k=1, 2, ..., the non-refracted X-ray component is decreased and the refracted X-ray component is increased in the X-rays to be detected through the second absorption grating 22. Especially, in the position of k=M/2, substantially only the refracted X-ray component is detected through the second absorption grating 22. After the position of M/2, on the contrary, the refracted X-ray component is decreased and the non-refracted X-ray component is increased in the X-rays to be detected through the second absorption grating 22.

Since the FPD 20 captures the image in each of the positions of k=0, 1, 2, ..., M−1, an M number of pixel data is obtained on each pixel 40. A method for calculating the phase shift amount $\psi$ of the intensity modulation signal of each pixel 40 from the M number of pixel data will be hereinafter described. When the second absorption grating 22 is in the position k, the pixel data $I_k(x)$ of each pixel 40 is represented by the following expression (10):

$$I_k(x) = A_0 + \sum_{n>0} A_n \exp\left[2\pi i \frac{n}{P_2}\left\{L_2\phi(x) + \frac{kP_2}{M}\right\}\right] \quad (10)$$

Wherein, x represents a coordinate of the pixel in the X direction, and $A_0$ represents the intensity of the incident X-rays, and $A_n$ represents a value corresponding to the contrast of the intensity modulation signal (n is a positive integer). $\phi(x)$ corresponds to the above refraction angle $\phi$ represented as a function of the coordinate x of the pixel 40.

With the use of the following expression (11), the refraction angle $\phi(x)$ is represented by the following expression (12):

$$\sum_{k=0}^{M-1} \exp\left(-2\pi i \frac{k}{M}\right) = 0 \quad (11)$$

$$\phi(x) = \frac{P_2}{2\pi L_2} \arg\left[\sum_{k=0}^{M-1} I_k(x)\exp\left(-2\pi i \frac{k}{M}\right)\right] \quad (12)$$

Wherein, "arg[ ]" means an argument of a complex number, and corresponds to the phase shift amount $\psi$. Therefore, the determination of the phase shift amount $\psi$ based on the expression (12) from the M number of pixel data (intensity modulation signals) obtained from each pixel 40 allows obtainment of the refraction angle $\phi(x)$ and the differentiation of the phase shift distribution $\Phi(x)$.

Figure 11:
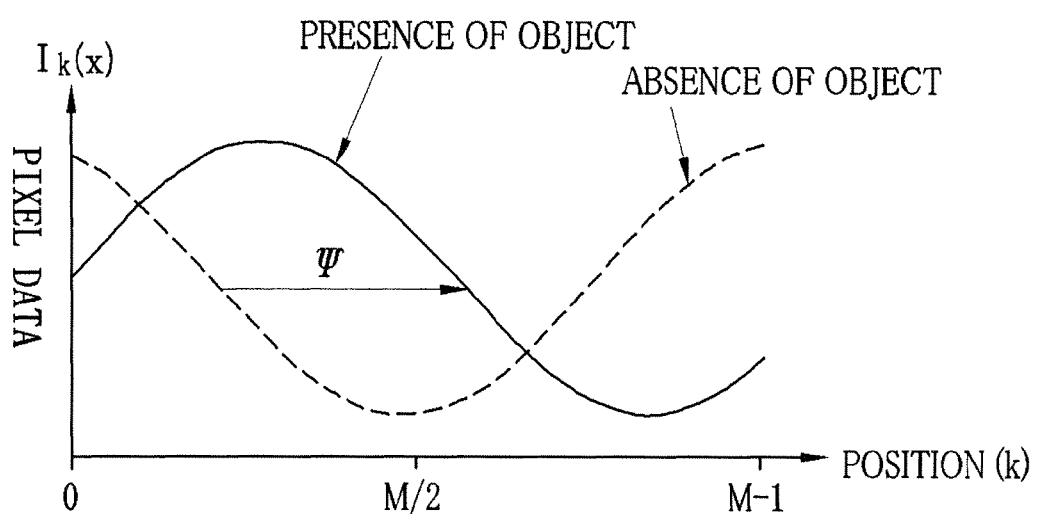
FIG. 11 is a graph of pixel data (intensity modulation signals) obtained by the fringe scanning technique.

To be more specific, taking the sliding position k of the second absorption grating 22 in a horizontal axis of a graph, the M number of pixel data obtained in each pixel 40 is plotted on the graph and fitted to a sine wave, as shown in FIG. 11, to obtain the intensity modulation signal, which periodically varies with the period of the grating pitch $P_2$. In FIG. 11, a dashed line represents the intensity modulation signal in the absence of the object B, and a solid line represents the intensity modulation signal in the presence of the object B. The phase difference between the wave formed intensity modulation signals corresponds to the above phase shift amount $\psi$.

Although the Y coordinate of each pixel 40 is not considered in the above description, carrying out similar calculations with respect to each Y coordinate allows obtainment of two-dimensional distribution $\psi(x,y)$ of the phase shift amounts along the X and Y directions. This two-dimensional distribution $\psi(x,y)$ of the phase shift amounts corresponds to the differential phase image. As is obvious from the above expressions (8) and (9), since the phase shift amount $\psi$ is proportionate to the refraction angle $\phi$, both of the phase shift amount $\psi$ and the refraction angle $\phi$ are physical values proportionate to the differentiation of the phase shift distribution $\Phi(x)$.

The image processor 14 integrates the differential phase image obtained above along an X axis, and produces the phase shift distribution $\Phi(x)$ of the object B. The phase shift distribution $\Phi(x)$ is written to the image storage 15 as the phase contrast image. The phase contrast image written to the image storage 15 is displayed on the monitor of the console 17.

In the first embodiment, the third absorption grating 25, the first absorption grating 21, and the second absorption grating 22 are aligned in this order, but the alignment order of the first to third absorption gratings 21, 22, and 25 is appropriately changeable. However, the third absorption grating 25 cannot be aligned lastly, because the small effective focus size of the X-ray source is necessary to produce the moiré pattern.

The use of the X-ray source 11 having the sufficiently small X-ray focus 11a can eliminate the need for provision of the third absorption grating 25. Also in this case, the alignment order of the first and second absorption gratings 21 and 22 is appropriately changeable in a like manner.

In this embodiment, the first and second absorption gratings 21 and 22 linearly project the X-rays that have passed through the slits, but may diffract the X-rays and produce the so-called Talbot effect (refer to International Publication No. WO2004/058070 corresponding to U.S. Pat. No. 7,180,979). In this case, however, the length $L_2$ between the first and second absorption gratings 21 and 22 has to be set at the Talbot distance. Also, in this case, a phase grating (phase diffraction grating) is usable instead of the first absorption grating 21. This phase grating projects to the second absorption grating 22 the fringe image (self image) produced by the Talbot effect.

In this embodiment, the object B is disposed between the X-ray source 11 and the first absorption grating 21. However, even if the object B is disposed between the first and second absorption gratings 21 and 22, the phase contrast image can be produced in a like manner.

Second Embodiment

Figure 12:
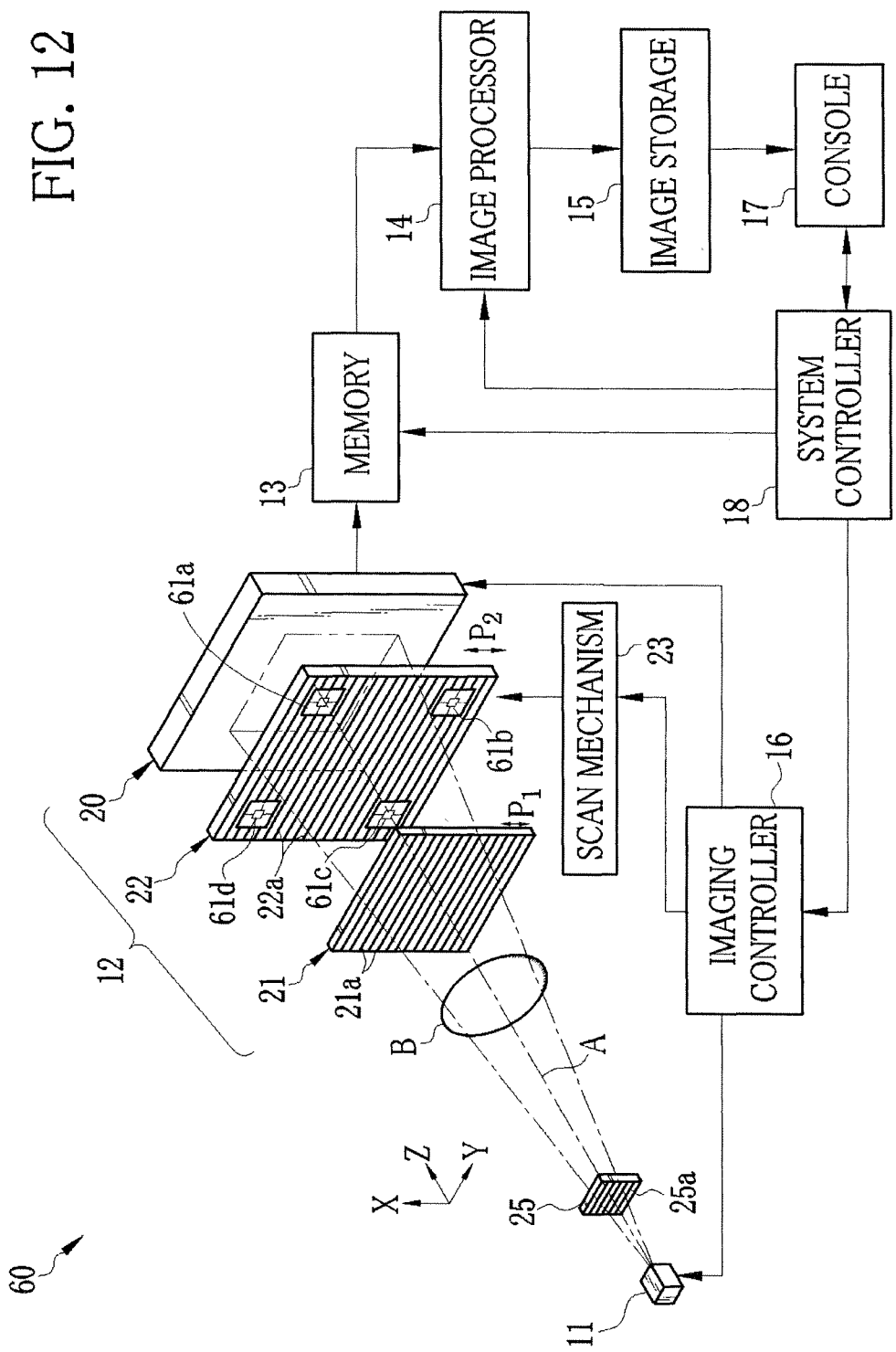
FIG. 12 is a schematic view of the X-ray image detector according to a second embodiment.
Figure 13:
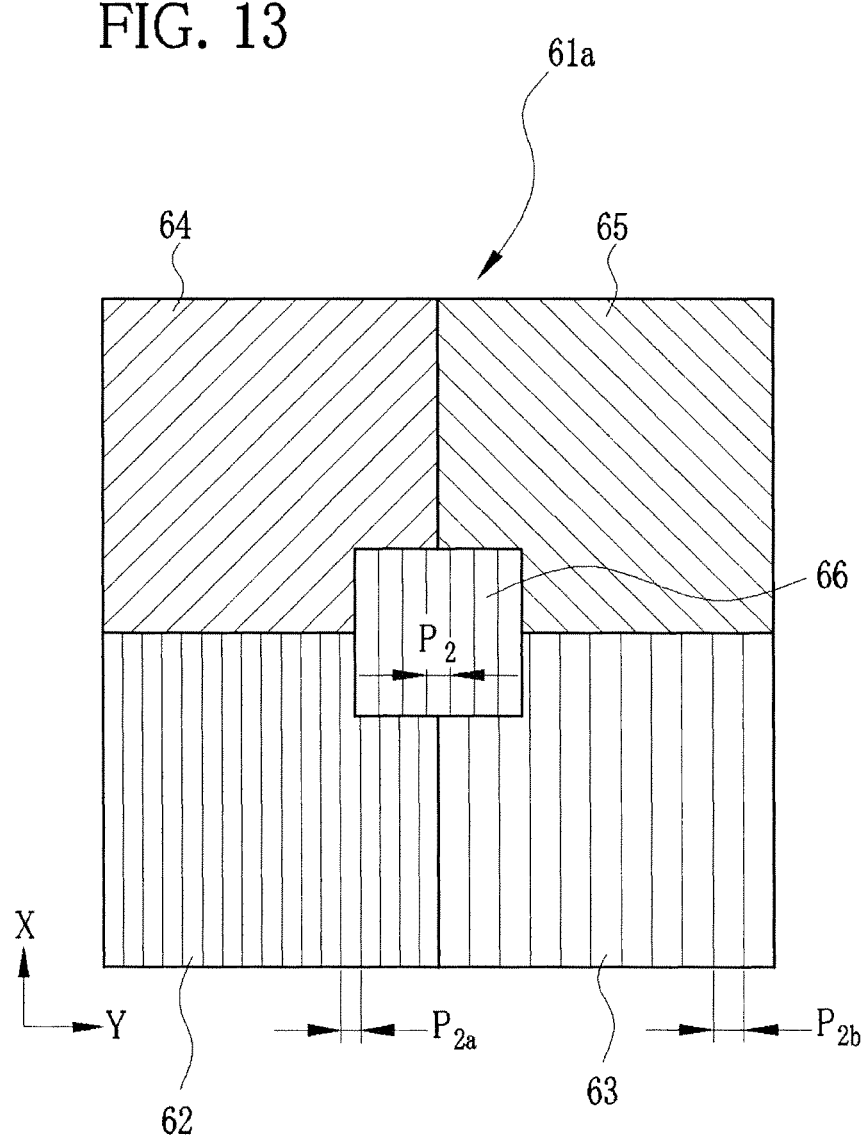
FIG. 13 is an explanatory view of an alignment section.

In a second embodiment, the grating has an alignment section for use in the position adjustment. The same reference numerals as those of the first embodiment refer to the same or similar components, and detailed description thereof will be omitted. As shown in FIG. 12, in an X-ray imaging system 60 according to the second embodiment, the second absorption grating 22 is provided with alignment sections 61a to 61d at each of four corners unused in the imaging. As shown in FIG. 13, the alignment section 61a has four areas divided along the X and Y axes passing through the center of the alignment section 61a, and first to fourth alignment patterns 62 to 65 are provided in the four areas. Also, a fifth alignment pattern 66 is provided in a middle area of the alignment section 61a. Since the alignment areas 61b to 61d are the same as the alignment area 61a, the detailed description thereof is omitted.

Each of the first to fifth alignment patterns 62 to 66 is a grid pattern. A grid pitch $P_{ea}$ of the first alignment pattern 62 is set narrower than the grating pitch $P_2$ of a grating pattern composed of the X-ray shield members 22a of the second absorption grating 22. A grid pitch $P_{2b}$ of the second alignment pattern 63 is set wider than the grating pitch $P_2$ of the grating pattern. The third alignment pattern 64 is inclined in the +θz direction relative to the grating pattern. The fourth alignment pattern 65 is inclined in the −θz direction relative to the grating pattern. The fifth alignment pattern 66 is the same as the grating pattern, and has a grid pitch of $P_2$.

To be more specific, if the grating pitch $P_2$ of the grating pattern is 5 μm, the grid pitch $P_{2a}$ of the first alignment pattern 62 is set at 4.8 μm, and the grid pitch $P_{2b}$ of the second alignment pattern 63 is set at 5.2 μm. The third and fourth alignment patterns 64 and 65 are inclined by one degree in the +θz and −θz directions, respectively.

The alignment patterns 62 to 66 produce moiré patterns in the X-rays that have passed through the alignment section 61a. Thus, checking the moiré patterns makes it possible to find out a state and a direction of positional deviation of the first to third absorption gratings 21, 22, and 25.

Figure 14:
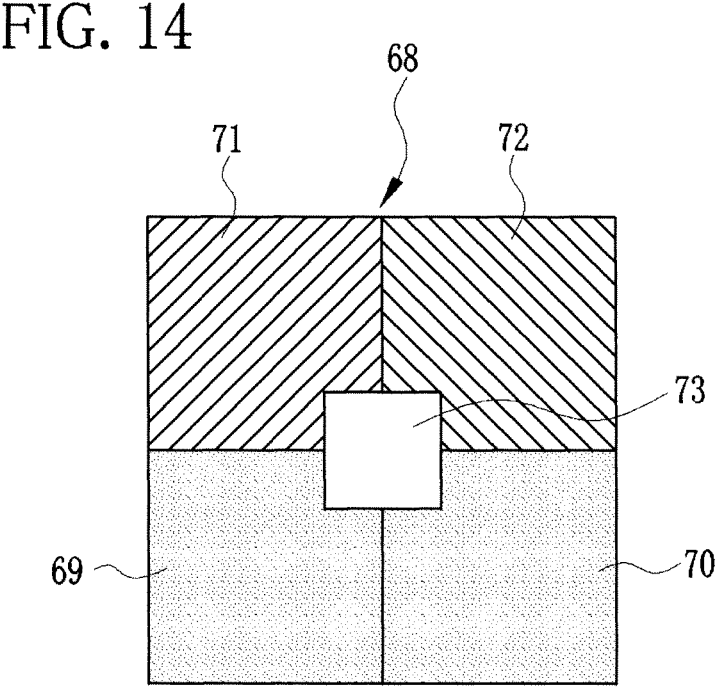
FIG. 14 is an explanatory view showing an image of the alignment section captured under conditions where the first to third absorption gratings are perfectly aligned.

If the first and second absorption gratings 21 and 22 are in optimal positions relative to each other, for example, the X-ray image detector 20 detects an image 68 of the alignment sections 61a to 61d as shown in FIG. 14. In this image 68, the moiré patterns appear in areas 69 to 72 corresponding to the first to fourth alignment patterns 62 to 65, while the moiré pattern does not appear in an area 73 corresponding to the fifth alignment pattern 66.

Figure 15:
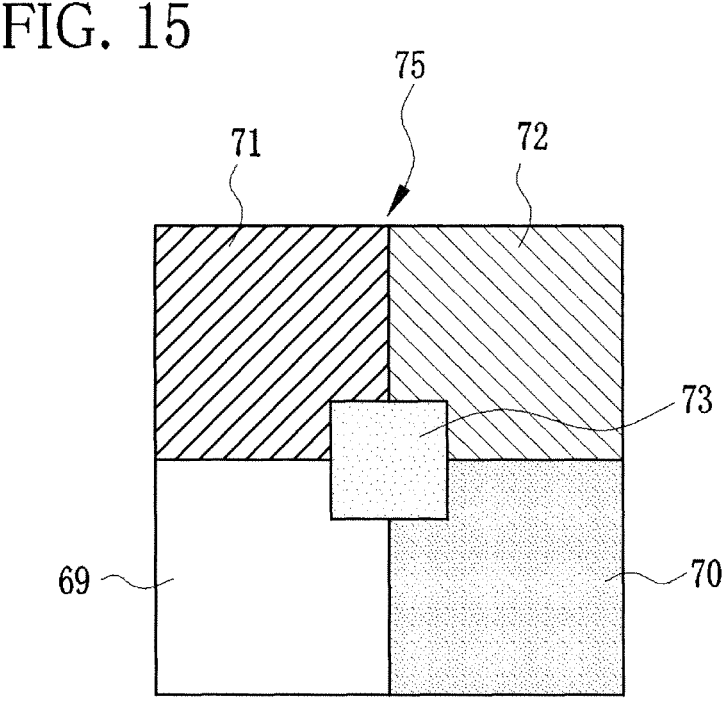
FIG. 15 is an explanatory view showing an image of the alignment section captured under conditions where the first to third absorption gratings deviate in a Z direction.

If the first absorption grating 21 deviates in the +Z direction from the second absorption grating 22, the X-ray image detector 20 detects an image 75 of the alignment sections 61a to 61d as shown in FIG. 15. In this image 75, the moiré patterns appear in areas 70 to 73 corresponding to the second to fifth alignment patterns 63 to 66, while the moiré pattern does not appear in the area 69 corresponding to the first alignment pattern 62. Although an illustration is omitted, if the first absorption grating 21 deviates in the −Z direction, the moiré pattern does not appear in the area 70 corresponding to the second alignment pattern 63. Thus, it is possible to easily identify the direction of the positional deviation along the Z axis.

Figure 16:
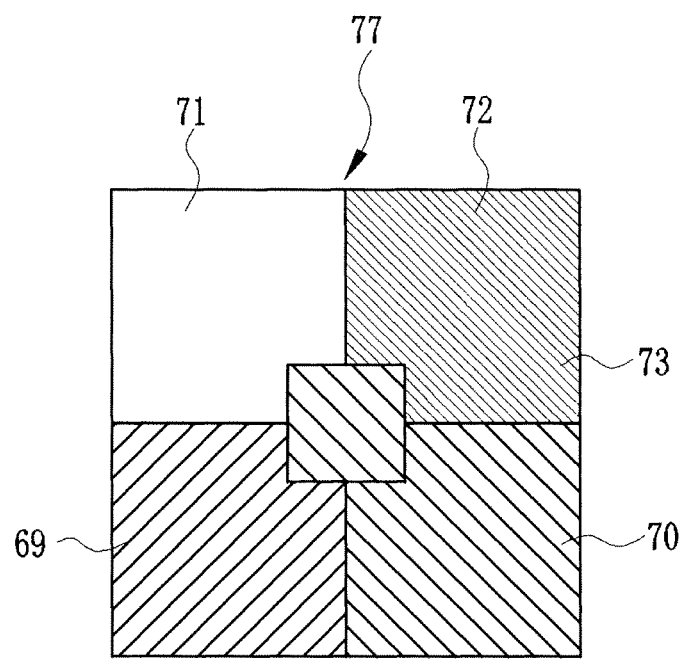
FIG. 16 is an explanatory view showing an image of the alignment section captured under conditions where the first to third absorption gratings deviate in a θZ direction.

If the first absorption grating 21 deviates in the +θz direction from the second absorption grating 22, the X-ray image detector 20 detects an image 77 of the alignment sections 61a to 61d as shown in FIG. 16. In this image 77, the moiré patterns appear in the areas 69, 70, 72, and 73 corresponding to the first, second, fourth, and fifth alignment patterns 62, 63, 65, and 66, respectively, while the moiré pattern does not appear in the area 71 corresponding to the third alignment pattern 64. If the first absorption grating 21 deviates in the −θz direction, the moiré pattern does not appear in the area 72 corresponding to the fourth alignment pattern 65. Thus, it is possible to easily identify the direction of the positional deviation about a θz axis.

Since the alignment sections 61a to 61d are provided in the four corners of the second absorption grating 22, comparing images of the alignment sections 61a to 61d makes it possible to easily identify the direction of the positional deviation of the first absorption grating 21 relative to the second absorption grating 22 about each of θx and θy axes. Although details will not be described, the third absorption grating 25 can be aligned with the second absorption grating 22 by use of images of the alignment sections 61a to 61d in a like manner as the first absorption grating 21.

Next, the alignment procedure of the first to third absorption gratings 21, 22, and 25 with use of the alignment sections 61a to 61d will be described. As shown in FIG. 17, in the X-ray imaging system 60, the second absorption grating 22 is firstly disposed in the Z axis (S11). The position of the second absorption grating 22 is adjusted in the θx and θy directions based on the dose of the X-rays having passed therethrough (S12), as in the case of the grating to be first aligned described in the first embodiment.

Then, the first absorption grating 21 is disposed in the Z axis of the X-ray imaging system 60 (S13), and the position of the first absorption grating 21 relative to the second absorption grating 22 is adjusted in the θz, θx, θy, and Z directions (S14). In this adjustment step, the X-ray image detector 20 detects the X-rays that have emitted from the X-ray source 11 and passed through the first and second absorption gratings 21 and 22.

In the images of the alignment section 61a to 61d detected by the X-ray image detector 20, as shown in FIGS. 14 to 16, the moiré pattern does not appear in at least one of the areas corresponding to the first to fifth alignment patterns 62 to 66, according to the direction of the positional deviation of the first absorption grating 21 relative to the second absorption grating 22. The area without the moiré pattern indicates the state and direction of the positional deviation of the first absorption grating 21. If necessary, the first absorption grating 21 is moved to an appropriate direction to correct the deviation.

By comparison among the images of the alignment sections 61a to 61d, the positional deviation of the first absorption grating 21 relative to the second absorption grating 22 is identified in the θx and θy directions. Thus, the first absorption grating 21 is rotated in such a direction as to cancel out the positional deviation. If there is no difference among the images of the alignment sections 61a to 61d, the first absorption grating 21 does not deviate in the θx and θy directions, and hence the first absorption grating 21 does not need to be adjusted in the θx and θy directions.

After the adjustment of the position of the first absorption grating 21, the third absorption grating 25 is disposed in the Z axis of the X-ray imaging system 60 (S15). Then, as in the case of the first absorption grating 21, the position of the third absorption grating 25 relative to the second absorption grating 22 is adjusted in the θz, θx, θy, and Z directions based on the images of the alignment sections 61a to 61d (S16).

According to the second embodiment, as described above, an amount of the positional deviation of the grating is identified without rotating the grating to be aligned second or later, in contrast to the first embodiment. This facilitates reduction in time for the alignment procedure. Only the second absorption grating 22 has the alignment sections 61a to 61d in the above embodiment, but the first and third absorption gratings 21 and 25 may have the alignment sections 61a to 61d too.

The first embodiment is predicated on the use of the X-ray source 11 for emitting the X-rays of the cone beam, but may use an X-ray source for emitting parallel X-rays. In this case, the above expressions (1), (2), (4), and (5) are modified into the following expressions (13) to (16), respectively:

$$P_2 = P_1 \tag{13}$$

$$D_2 = D_1 \tag{14}$$

$$Z = m\frac{P_1^2}{\lambda} \tag{15}$$

$$L_2 < \frac{P_1^2}{\lambda} \tag{16}$$

The present invention is applicable to various types of radiation imaging systems for medical diagnosis, industrial use, nondestructive inspection, and the like. As the radiation, gamma rays or the like are usable other than the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An alignment method of plural diffraction gratings used in an X-ray radiation imaging system for capturing a phase contrast image, the X-ray radiation imaging system including an X-ray radiation source for emitting an X-ray radiation, an X-ray radiation image detector for detecting an image carried on the X-ray radiation, and the diffraction gratings disposed between the X-ray radiation source and the X-ray radiation image detector, the alignment method comprising:

disposing one of the plural diffraction gratings to be first aligned in a Z axis orthogonal to a detection surface of the X-ray radiation image detector;

after the disposition of the diffraction grating to be first aligned, while the diffraction grating to be first aligned is rotated in a θx direction about an X axis orthogonal to the Z axis and in a θy direction about a Y axis orthogonal to the Z and X axes, measuring a dose of the X-ray radiation having passed through the diffraction grating to be first aligned, and locating the diffraction grating to be first aligned in such a position in the θx and θy directions that the dose of the X-ray radiation is maximized;

after the location of the diffraction grating to be first aligned, disposing in the Z axis another one of the plural diffraction gratings to be aligned second or later, so that the X-ray radiation forms a moiré pattern;

after the disposition of the diffraction grating to be aligned second or later, while the diffraction grating to be aligned second or later is rotated in the θx and θy directions, detecting the moiré pattern by the X-ray radiation image detector, and locating the diffraction grating to be aligned second or later in such a position in the θx and θy directions that a frequency of the moiré pattern becomes uniform; and adjusting at least one of a relative position among the plural diffraction gratings along a direction of the Z axis and a relative position among the plural diffraction gratings in a θz direction about the Z axis, so that the X-ray radiation image detector detects removal of the moiré pattern.

2. The alignment method according to claim 1, wherein in the adjustment, at least one of the relative position among the plural diffraction gratings along the direction of the Z axis and the relative position among the plural diffraction gratings in the θz direction is adjusted, so that a period of the moiré pattern becomes larger than a detection area of the X-ray radiation image detector.

3. The alignment method according to claim 1, wherein the plural diffraction gratings include a first diffraction grating for passing the X-ray radiation and producing a fringe image, and a second diffraction grating for applying intensity modulation to the fringe image in each of plural relative positions out of phase with one another with respect to a periodic pattern of the fringe image.

4. The alignment method according to claim 3, wherein the plural diffraction gratings further include a third diffraction grating disposed between the X-ray radiation source and the first diffraction grating, and the third diffraction grating partly blocks the X-ray radiation emitted from the X-ray radiation source and produces plural line sources.

5. The alignment method according to claim 4, wherein the third diffraction grating is to be aligned first or second.

6. The alignment method according to claim 1, wherein in the disposition of the diffraction grating to be aligned second or later, the diffraction grating to be aligned second or later is disposed so as to deviate from a target position in the direction of the Z axis or in the θz direction.

* * * * *